United States Patent [19]

Lindstrom

[11] 4,202,875

[45] * May 13, 1980

[54] RECEPTOR FOR BIOCHEMICAL ASSAY SYSTEM

[75] Inventor: Jon M. Lindstrom, Del Mar, Calif.

[73] Assignee: The Salk Institute for Biological Studies, San Diego, Calif.

[*] Notice: The portion of the term of this patent subsequent to Jul. 5, 1994, has been disclaimed.

[21] Appl. No.: 888,347

[22] Filed: Mar. 20, 1978

[51] Int. Cl.$^2$ ...................... G01N 33/16; A61K 43/00
[52] U.S. Cl. ...................................... 424/1; 23/230.3; 23/230 B; 23/920; 424/1.5
[58] Field of Search ................... 23/230.3, 230 B, 920; 424/1, 1.5, 12

[56] References Cited

U.S. PATENT DOCUMENTS 4,033,722   7/1977   Lindstrom ........................... 23/230.3

OTHER PUBLICATIONS

Fambrough et al., "Neuromuscular Junction in Myasthenia Gravis Decreased Acetylcholine Receptors", Science, vol. 182, Oct. 1973, pp. 293–295.

Almon et al., "Serum Globulin in Myasthenia Gravis: Inhibition of Bungarotoxin to Acetylcholine Receptors", Science, vol. 186, No. 4158, Oct. 1974, pp. 55–57.

*Primary Examiner*—Arnold Turk
*Attorney, Agent, or Firm*—Fitch, Even & Tabin

[57] ABSTRACT

Components for a biochemical assay system for diagnosis of myasthenia gravis in humans. Acetylcholine receptor protein is extracted from non-human mammalian fetal muscle tissue. The acetylcholine receptor protein is then used in a bio-assay system as a complex of the acetylcholine receptor protein and a toxin labeled with a radioactive isotope.

3 Claims, No Drawings

RECEPTOR FOR BIOCHEMICAL ASSAY SYSTEM

The present invention relates generally to components for a biochemical assay system for use in medical diagnosis. More particularly, the present invention relates to a bio-assay for myasthenia gravis containing such components and to the diagnosis of myasthenia gravis in humans.

In recently issued U.S. Pat. No. 4,033,722 of Lindstrom, a bio-assay system for myasthenia gravis was disclosed. In accordance with this patent, a complex of acetylcholine receptor protein (AChR) and a toxin labeled with a radioactive isotope was prepared. The AChR was extracted from human muscle tissue, since non-human mammalian muscle tissue provided AChR which was a less effective antigen for human antibodies. While AChR derived from human muscle is highly effective to provide the complex of AChR and radioactive toxin, the procurement of human muscle is difficult. It would be desirable to provide AChR from a readily available source which is an effective antigen for human antibodies.

Accordingly, it is a principal object of the present invention to provide acetylcholine receptor protein from a non-human source which is effective to provide a serum-assay system for diagnosis of myasthenia gravis. It is another object of the invention to provide a serum-assay system for diagnosis of myasthenia gravis which utilizes acetylcholine receptor protein from sources other than human muscle and to provide a diagnostic method utilizing such non-human acetylcholine receptor protein which is highly selective and which can distinguish myasthenia gravis from other diseases.

Generally, in accordance with various features of the present invention, acetylcholine receptor protein (AChR) is extracted from non-human mammalian fetal muscle tissue. The fetal muscle tissue of any domestic animal can be used to provide AChR for use in the bio-assay system of the present invention. Particularly preferred, for reasons of availability, is the fetal tissue of those domestic mammalian animals which are used to provide meat for human consumption, i.e., calves, lambs, kids and pigs.

The AChR is extracted from the fetal muscle tissue in accordance with the procedures set forth in U.S. Pat. No. 4,033,722.

One volume of minced muscle tissue is homogenized in a high shear blender at 4° C. in 4 volumes of an aqueous salt solution. The aqueous salt solution is 0.1 M NaCl, 0.01 M sodium phosphate (pH 7.0), and 0.01 M $NaN_3$. The homogenized muscle tissue is then centrifuged for 30 minutes at $10^5 \times g$. The pellet resulting from the centrifugal separation is extracted with 2 volumes of the above-described salt solution containing 2 percent by weight of a surfactant. A surfactant available under the tradename Triton X-100 from Sigma Company is preferred. The extraction is effected by shaking the residue for 1 hour in the solution. After extraction, the mixture is centrifuged for 1 hour at $10^5 \times g$. The supernate from the centrifugation contains AChR at a level of 2 to $8 \times 10^{-10}$ M.

The toxin used in the complex may be any of the known toxins which bind to AChR. Such toxins are derived from cobras or sea snakes. Naja naja siamensis toxin and α bungarotoxin from Bungarus multicinctus have been found to be particularly effective and are preferred.

Purified toxin is labeled with any suitable radioactive isotope in accordance with standard procedures. $I^{125}$ is preferred for reasons of cost and availability. The toxin is labeled with $I^{125}$ according to standard techniques using chloramine T as follows: To 5 mci of carrier-free $I^{125}$ ($2.4 \times 10^{-9}$ moles) is added 10 microliters of 0.1 M sodium phosphate buffer (pH 7.0) followed by sufficient 0.1 M HCl to neutralize the NaOH in which the $I^{125}$ is shipped. Toxin ($2.4 \times 10^{-8}$ moles) and NaI ($2.4 \times 10^{-8}$ moles) are added in 40–50 microliters of 0.1 M sodium phosphate (pH 7.0) to the neutralized $I^{125}$. Chloramine T is added (10 microliters containing $2.8 \times 10^{-8}$ moles) and the solution is agitated for 10 minutes. The solution along with 100 microliters of buffer is applied to a Sephadex G 25 column ($1 \times 10$ cm). A complex of $I^{125}$-toxin elutes in the void volume along with 86 percent of the radioactivity. When the above procedure is repeated but NaI is omitted and the chloramine T is reduced to $0.93 \times 10^{-8}$ moles, the incorporation of $I^{125}$ is 100 percent. Both methods produce a complex of $I^{125}$-toxin effective to label AChR.

AChR is complexed with the $I^{125}$-toxin by incubation with excess $I^{125}$-toxin for several hours. The $I^{125}$-toxin bound to AChR is measured by using a Sephadex G-200 column (10 cm $\times$ 1 cm) which separates $I^{125}$-toxin-AChR complexes from free $I^{125}$-toxin. Since AChR is present as a minor component of the muscle extract, it is highly specific labeling of AChR by $I^{125}$-toxin that gives the specific antigen used in this assay.

The concentration of serum antibodies from a blood sample of a patient which couple to the AChR complex is measured by a double precipitin assay. AChR complexed with $I^{125}$-toxin from either Naja naja siamensis or Bungarus multicinctus is incubated with diluted serum. Antibodies found in sera of patients with myasthenia gravis are attached to AChR during the incubation. The resulting complex of antibody-AChR-$I^{125}$-toxin is precipitated along with other immunoglobulin in the serum by addition of anti-immunoglobulin. Radioactivity in the resulting precipitate is then measured. Radioactivity in a precipitate obtained by omitting AChR from the reaction mixture is substracted from this value to correct for radioactivity nonspecifically trapped in the pellet. Using the known specific radioactivity of $I^{125}$-toxin the corrected value for radioactivity in the pellet is converted to a titer expressed in moles of toxin binding sites bound per liter of serum. Virtually all patients having myasthenia gravis which were tested had high titers, whereas patients which did not have myasthenia gravis had low or no titers.

In a specific example of the present invention, the antibody-AChR titer of various human subjects known to be suffering from myasthenia gravis was determined. AChR was extracted from human muscle tissue, rat muscle tissue, calf fetal muscle tissue, eel and torpedo.

Complexes of the AChR and $I^{125}$-toxin were prepared in accordance with the method described above. Triplicate 1 ml aliquots of the AChR ($5 \times 10^{-10}$ M) from the respective sources were labeled in the presence of the $I^{125}$-toxin ($1 \times 10^{-9}$ M) by incubation at 4° C. for 4 hours. Triplicate 1 ml aliquots of $I^{125}$-toxin ($1 \times 10^{-9}$ M, Naja naja siamensis) were also prepared to serve as a control. 5 microliters of serum obtained from the blood of the patient were added to each tube. After overnight incubation at 4° C., goat anti-human gamma-globulin (15 percent $Na_2SO_4$ cut) was added. The amount of goat serum used was that which gave a maximum precipitate when tested with 5 microliters of normal human serum (usually about 15 microliters). After 4 hours incubation at 4° C. the tubes were centrifuged, the pellet was washed once and the radioactivity of the pellet determined. The radioactivity of the $I^{125}$-toxin blanks was substracted from the average value for the tubes containing AChR. The titer in terms of the average moles of the toxin binding sites which were bound by antibodies per liter was determined in accordance with the following formula:

$$\frac{(cpm/\text{assay pellet}) \times \frac{10^6 \text{ microliters/liter}}{5 \text{ microliters serum/assay}}}{cpm/\text{mole toxin} - I^{125}} = \frac{\text{moles toxin binding sites bound}}{\text{liter serum}}$$

where: Cpm=counts of radioactivity per minute. The results are set forth below in Table 1.

TABLE I

| Serum From Patient Number | Human ($\times 10^{-9}$M) | Antibody Titers Against AChR from Various Species | | | | | |
|---|---|---|---|---|---|---|---|
| | | Monkey | Fetal Calf | Mouse BC3H-1 | Rat | Torpedo | Eel |
| | | (% of titer against human AChR) | | | | | |
| 1 | 1,313 | 54 | 22. | 3.5 | 0.11 | 0.20 | 0 |
| 2 | 1,293 | 52 | 16. | 3.4 | 0.10 | 0.06 | 0 |
| 3 | 1,256 | 50 | 19. | 2.9 | 0.10 | 0.16 | 0 |
| 4 | 1,254 | 66 | 18. | 4.8 | 0.12 | 0.14 | 0 |
| 5 | 1,254 | 64 | 17. | 4.0 | 0.12 | 0.18 | 0 |
| 6 | 1,160 | 48 | 18. | 4.4 | 0.24 | 0.71 | 0 |
| 7 | 1,069 | 59 | 21. | 5.9 | 0.29 | 1.00 | 0 |
| 8 | 557 | 18 | 20. | 1.3 | 0 | .09 | 0 |
| 9 | 505 | 89 | 26. | 8.0 | 0.47 | .22 | 0 |
| 10 | 499 | 60 | 28. | 1.7 | 0.19 | 1.00 | 0 |
| 11 | 432 | 45 | 25. | 2.1 | 2.1 | 1.4 | 0 |
| 12 | 379 | 73 | 69. | 0.30 | .36 | 2.3 | 0 |
| 13 | 239 | 58 | 2.5 | 0.39 | 8.4 | 1.6 | 0 |
| 14 | 228 | 60 | 2.9 | 0.17 | 0 | 1.2 | 0 |
| 15 | 216 | 59 | 6.1 | 3.4 | 0.54 | 2.4 | 0 |
| 16 | 99.5 | 55 | 6.3 | 1.8 | 1.1 | 2.2 | 0 |
| 17 | 99.2 | 89 | 5.4 | 4.1 | 4.4 | 2.2 | 0 |
| 18 | 92.4 | 13 | 23.0 | 0.54 | 0 | 3.8 | .8 |
| 19 | 63.8 | 75 | 4.3 | 6.6 | 5.7 | 0 | 0 |
| 20 | 57.3 | 37 | 18. | 15. | 12. | 2.4 | 0 |
| 21 | 55.7 | 18 | 7.1 | 8.1 | 4.6 | 5.9 | .9 |
| 22 | 44.6 | 6 | 1.1 | 2.5 | 1.9 | 2.7 | 0 |
| 23 | 29.6 | 10 | 3.5 | 6.0 | 3.0 | 14.0 | 2.7 |
| 24 | 12.1 | 14 | 5.1 | 12. | 4.5 | 4.6 | 0 |
| Average | 509 | 49 | 16. | 4.3 | 2.1 | 2.1 | 0 |

It can be seen that the AChR from fetal calf has an average effectiveness which is 16 percent of that of AChR derived from human muscle tissue. This level of effectiveness is considered adequate to utilize the fetal calf muscle tissue in the bio-assay system. While the fetal calf muscle tissue does not provide AChR which is as effective as human muscle tissue or monkey muscle tissue, the effectiveness is sufficient to permit use of the fetal calf muscle tissue in the bio-assay system.

What is claimed is:

1. In a biochemical assay system comprising a complex of acetylcholine receptor protein derived from muscle tissue with toxin labeled with a radioactive isotope, the improvement wherein the acetylcholine receptor protein is derived from non-human mammalian fetal muscle tissue.

2. A biochemical assay system in accordance with claim 1 wherein said acetylcholine receptor protein is derived from the fetal muscle tissue of calves, lambs, kids or pigs.

3. A biochemical assay system in accordance with claim 2 wherein said acetylcholine receptor protein is derived from calf fetal muscle tissue.

* * * * *

UNITED STATES PATENT AND TRADEMARK OFFICE
CERTIFICATE OF CORRECTION

PATENT NO. : 4,202,875
DATED : May 13, 1980
INVENTOR(S) : Jon M. Lindstrom

It is certified that error appears in the above-identified patent and that said Letters Patent are hereby corrected as shown below:

Column 1, line 41, after "fetal" insert --muscle--.

Column 1, line 51, after "phosphate" insert --buffer--.

Signed and Sealed this

Twenty-third Day of September 1980

[SEAL]

Attest:

SIDNEY A. DIAMOND

Attesting Officer

Commissioner of Patents and Trademarks